United States Patent [19]
Minkkinen et al.

[11] Patent Number: 5,720,929
[45] Date of Patent: *Feb. 24, 1998

[54] DEVICE FOR CATALYTIC DEHYDROGENATION OF A $C_{2+}$ PARAFFINIC CHARGE COMPRISING MEANS FOR INHIBITING THE FREEZING OF WATER IN THE EFFLUENT

[75] Inventors: Ari Minkkinen, Saint Nom La Breteche; Jean-Pierre Burzynski, Sainte-Foy-Les Lyon; Joseph Larue, Chambourcy, all of France

[73] Assignee: Institut Francais Du Petrole, Rueil Malmaison, France

[*] Notice: The term of this patent shall not extend beyond the expiration date of Pat. No. 5,711,919.

[21] Appl. No.: 472,650

[22] Filed: Jun. 7, 1995

Related U.S. Application Data

[62] Division of Ser. No. 148,274, Nov. 8, 1993, Pat. No. 5,489,725.

[30] Foreign Application Priority Data

Nov. 6, 1992 [FR] France ................... 92/13.516

[51] Int. Cl.$^6$ ................... B01J 8/04; B01J 8/08; C07C 5/333
[52] U.S. Cl. ................... 422/190; 422/217; 422/234; 422/236; 585/655; 585/654; 585/324
[58] Field of Search ................... 422/190, 216, 422/217, 234, 236; 585/655, 654, 324

[56] References Cited

U.S. PATENT DOCUMENTS

| | | | |
|---|---|---|---|
| 3,536,775 | 10/1970 | Hutson, Jr. et al. | 585/868 |
| 3,663,641 | 5/1972 | Hanson | 585/868 |
| 4,381,417 | 4/1983 | Voxa et al. | 585/655 |
| 4,663,493 | 5/1987 | Vora et al. | 585/655 |
| 4,695,662 | 9/1987 | Vora | 585/324 |
| 5,214,225 | 5/1993 | Hall et al. | 585/654 |
| 5,220,093 | 6/1993 | Gartside et al. | 585/661 |
| 5,254,788 | 10/1993 | Gartside et al. | 585/659 |
| 5,491,274 | 2/1996 | Minkkinen et al. | 585/655 |

FOREIGN PATENT DOCUMENTS

| | | |
|---|---|---|
| 0 007 750 | 2/1980 | European Pat. Off. |
| 596799 | 5/1994 | European Pat. Off. |

Primary Examiner—Nina Bhat
Attorney, Agent, or Firm—Millen, White, Zelano, & Branigan, P.C.

[57] ABSTRACT

A device for the catalytic dehydrogenation of a $C_{2+}$ paraffinic hydrocarbon charge is applicable to the synthesis of methyl tert-butyl ether. Effluent coming from the dehydrogenation reactor and containing olefins and water is cooled in at least one heat exchanger (41), saturated with water in a column (3) and sent to a stripping column (10) where it is at least partly put in contact with a recycled aqueous liquid phase containing a solvent, preferably methanol. The compressed gaseous effluent in which the water is thereby inhibited from freezing by the methanol is cooled in a heat exchanger (13) then separated in separator (8) into olefins and into hydrogen. An aqueous liquid phase with methanol is decanted at (8) and recycled in column (10).

9 Claims, 2 Drawing Sheets

DEVICE FOR CATALYTIC DEHYDROGENATION OF A $C_{2+}$ PARAFFINIC CHARGE COMPRISING MEANS FOR INHIBITING THE FREEZING OF WATER IN THE EFFLUENT

CROSS-REFERENCE TO RELATED APPLICATION

This is a division of the application Ser. No. 08/148,274 filed Nov. 8, 1993 now U.S. Pat. No. 5,489,725.

This application is related to a concurrently filed application entitled PROCESS AND DEVICE FOR CATALYTIC DEHYDROGENATION OF $C_{2+}$ PARAFFINIC CHARGE COMPRISING A SELF-COOLING SYSTEM Ser. No. 08/148,267, now U.S. Pat. No. 5,491,274 based on French Application No. 92/13.515, filed Nov. 6, 1992, by Ari Minkkinen and Jean Pierre Burzynski.

BACKGROUND OF THE INVENTION

The invention relates to a process and associated apparatus for the catalytic dehydrogenation of a $C_{2+}$ paraffinic hydrocarbon charge. It relates more particularly to the inhibition of freezing of the water contained in the effluent before the cooling and the separation of the effluent.

U.S. Pat. Nos. 3,536,775 and 3,663,641 describe a process for removing, by contact with water, the oxygen contained in a butadiene cut obtained by an oxidizing dehydrogenation of a butene cut. Patent EP-A-7750 describes a process for removing the water contained in nonolefinic light hydrocarbons such as natural gas, liquefied gases, gasolines or kerosene, by adding aqueous methanol. Under these conditions, a hydrocarbon liquid phase containing methanol which prevents the formation of hydrates is obtained. Moreover, the methanol is not recovered from the aqueous liquid phase.

Finally, U.S. Pat. No. 3,663,641 illustrates the technological background.

It is known that a number of industrial processes using low pressure catalytic reactions operate in a hydrogen environment in which the partial pressure of hydrogen is assured by a recycling of a hydrogen-rich gas contained in a reaction effluent and which has been separated from the hydrocarbons.

This is the case in particular of a catalytic dehydrogenation process of LPG's containing propane, butane and isobutane to produce mono-olefins which serve as an intermediate for the production of fuel with high octane number. In the case of the dehydrogenation of isobutane, the isobutene produced can react with methanol to produce methyl tertbutyl ether, an additive that can be used in gasolines.

The prior art is illustrated by U.S. Pat. Nos. 4,381,418 and 4,381,417. In such processes, the reaction is performed in a continually regenerated catalytic reactor operating at very low pressure (slightly higher than the atmospheric pressure or under vacuum) and at temperatures of 500° C. to 600° C.

The recycled hydrogen and the hydrogen produced assure sufficient partial pressure of the hydrogen to inhibit the formation of coke and thereby to maintain the stability of the catalyst. Thus, a satisfactory conversion to a higher range of temperatures reaching, for example, 600° C., is achieved. Generally, the low pressure effluent delivered by the dehydrogenation reaction zone is cooled first of all by heat exchange with the gas charge then with water, at a suitable temperature before the vapor pressure of the effluent is effectively raised, in a conventional piece of compression equipment, at a higher pressure, which makes possible the separation of the hydrogen and the hydrocarbon compounds of the effluent. These conventional exchangers and other air coolers increase the counterpressure of the reaction system, which negatively affects the conversion rate. To eliminate these drawbacks, it has been attempted to use heat exchangers with slight pressure drop and with direct cooling with circulating cooling (quenching) liquids, but without great success.

The separation of the hydrogen from the hydrocarbons of the effluent must be performed at a pressure higher than that prevailing in the reaction zone. Moreover, to condense the hydrocarbons in the gas mixture constituting the effluent and containing hydrogen, it is necessary to cool to a temperature lower than that which conventional air or water heat exchangers can achieve.

Since a cooling below 0° C. is required for the separation of the hydrogen and the hydrocarbon compounds, the water present in the compressed effluent must be removed down to a concentration limit such that there is no freezing, to prevent the obstruction of the cooling equipment. For this purpose, 3 Å molecular sieves are used to displace the water of the effluent before the cooling step (1 Å $=10^{-10}$ m).

However, the adsorption beds with molecular sieves also impose pressure drops on the compression effluent due not only to the adsorption beds themselves but to systems of filters downstream from these beds which pick up the dust from molecular sieves that can obstruct the passage of the effluent in the cooling equipment. Furthermore, the molecular sieves involve periods of adsorption of the water followed by periods of regeneration which are difficult to control.

SUMMARY OF THE INVENTION

An object of the invention is to eliminate the drawbacks mentioned above.

Upon further study of the specification and appended claims, further objects and advantages of this invention will become apparent to those skilled in the art.

The invention therefore relates to a process for catalytic dehydrogenation of a $C_{2+}$ paraffinic hydrocarbon charge comprising a step of dehydrogenating said charge in gas phase, optionally in the presence of hydrogen, delivering a dehydrogenation gaseous effluent comprising water, hydrogen, olefinic hydrocarbons and unconverted paraffinic hydrocarbons, at least one step of cooling the effluent, a step of compressing the cooled effluent at a suitable pressure, a step of inhibiting freezing of the water contained in the compressed effluent, a step of cooling the compressed effluent in a heat exchanger, a step of separating the compressed and cooled effluent in a separation zone under suitable conditions and a step of recovering hydrogen and hydrocarbons, for the most part olefinic.

More specifically, the process is characterized in that at least one part of the cooled effluent is saturated with water under suitable conditions in a saturation zone by direct contact with a mixture of liquid phases containing for the most part water, before or after the compression step, and the step of inhibiting the water in the effluent is performed:

(a) by contacting in a stripping zone and under suitable conditions at least one part of the effluent that is compressed and saturated with water with a recycled liquid phase containing both water and a solvent in suitable proportions, said solvent being a nonhydrocarbon organic compound, normally liquid, other than water, said compound being at least partially water-miscible and distillable at a temperature lower than that of the boiling temperature of the water, to obtain a gas phase charged with solvent and effluent and an aqueous liquid phase essentially rid of solvent;

(b) by introducing the gas phase that is charged with solvent and effluent into the remaining part of the effluent that is compressed and saturated with water, when the whole of the effluent that is compressed and saturated with water has not been put in contact with the recycled liquid phase;

(c) by making the gas phase that is charged with solvent and effluent of step (b), or of step (a) when step (b) is not necessary, circulate in said heat exchanger during the cooling step;

(d) by separating in the separation zone a decanted liquid phase containing water and solvent with a suitable concentration and (e) by recovering and by recycling the decanted liquid phase of step (d) to said stripping column of step (a).

By performing the water saturation of the effluent upstream from the compression device, a direct quenching of the effluent is advantageously performed, and the presence of air coolers before the compression is thereby avoided. Furthermore, most of the impurities contained in the effluent are eliminated, which, moreover, eliminates introducing a step of washing the supply upstream from the MTBE unit. Finally, the pressure drops upstream from the compressor are minimized.

By performing the water saturation of the effluent downstream from the compression device according to a variant of the process, a direct quenching of the effluent is also performed and most of the impurities contained in the effluent are also eliminated with the advantages described above.

According to a characteristic of the process, it is possible to perform effectively the saturation of the cooled effluent by introducing the aqueous liquid phase recovered from the stripping column and a recycled aqueous phase recovered at the bottom of the saturation zone at the upper part of the saturation zone, by introducing the cooled effluent at the lower part of the saturation zone, by achieving a direct countercurrent contact with the effluent with the mixture of aqueous phases through a suitable packing, by recovering the aqueous phase at the bottom of the saturation zone that is recycled, after having cooled it at least once, in the upper part of said zone, and the water-saturated and cooled effluent is recovered in the upper part of the saturation zone.

In general, the mixture of aqueous phases introduced into the saturation zone is at a temperature of −10° C. to +90° C. It can advantageously contain 1–15% of an alkaline metal hydroxide and preferably of soda.

The temperature of the saturation column is generally 0° C. to 100° C. and advantageously 20° C. to 50° C. The procedure is performed usually in this column under a pressure able to go from the atmospheric pressure to 3 absolute bars and more particularly from the atmospheric pressure to 1.5 absolute bars, when the column for saturating the water effluent is placed between the dehydrogenation reactor and the equipment for compressing the effluent. In the case where it is located after the compression of the effluent, the saturation column can operate under a pressure of 3 to 35 absolute bars and preferably 8 to 15 absolute bars. The pressure in the saturation column can therefore vary from 1 to 35 absolute bars (1 bar=$10^5$ Pa).

The stripping of the solvent in the stripping column is generally performed at a temperature of 10° C. to 150° C., preferably 80° C. to 120° C. under a pressure of 3 to 35 absolute bars and preferably 10 to 15 absolute bars.

The step of cooling the effluent, performed by a self-cooling device (evaporation of the liquid charge with or without recycled hydrogen) or by an external cooling device, can be performed at a temperature of 0° C. to −85° C., preferably −20° C. to −40° C. under a pressure of 3 to 35 absolute bars.

Finally, the separation of the effluent into hydrogen, into olefins and into the water and methanol liquid phase which is decanted is performed generally under 3 to 35 absolute bars, preferably under 8 to 12 absolute bars and at a temperature of 0° C. to −100° C. and, more specifically, −20° C. to −40° C.

According to a characteristic of the process, to perform effectively the stripping of the solvent in the stripping column, it is possible to introduce 1–100% by weight of the compressed effluent as stripping fluid and preferably 10–50%.

This stripping column usually comprises a preferably structured packing, with height equivalent to at least 1 theoretical plate, for example, 1 to 20 and advantageously 10 to 15 plates. These conditions combined with the introduction of a variable proportion of effluent into the stripping column cause the water recovered at the bottom of the stripping column and recycled at the input of the saturation zone to be able to contain at most 10,000 ppm of solvent, advantageously less than 2000 ppm and preferably 50–500 ppm.

According to another characteristic of the process, the concentration of methanol in the water-methanol decanted phase coming from the step of cooling the effluent which is introduced into the stripping column is generally 20–80% by weight, and preferably 50–65%. Generally, the density of the solvent is measured in the water constituting the decanted phase, which makes it possible to obtain its concentration and by comparison with a reference value stored in a microcomputer, it is possible to adjust this concentration to the desired level by adding a flow containing the solvent in the compressed effluent.

This flow can advantageously be the solvent or the wash waters (methanol) of a unit downstream from production of methyl tert-butyl ether.

The solvent used must be at least partially miscible with water. Preferably, it must have a boiling temperature less than that of the water or form with the water an azeotrope whose boiling temperature is less than that of water, to be able to be entrained by the gas phase constituting the effluent during the step of putting in contact the process. It must also be not very soluble in the hydrocarbons.

This solvent can advantageously be methanol and ethanol and preferably methanol because of its low cost. It can also be selected, for example, from the following solvents: methyl propyl ether, ethyl propyl ether, dipropyl ether, methyl tert-butyl ether, dimethoxymethane, dimethoxyethane, ethanol, methoxyethanol, propanol.

BRIEF DESCRIPTION OF THE DRAWINGS

Various other objects, features, and attendant advantages of the present invention will be more fully appreciated as the same becomes better understood when considered in conjunction with the accompanying drawings in which like reference characters designate the same or similar parts throughout the several views, and wherein.

Figure 1:
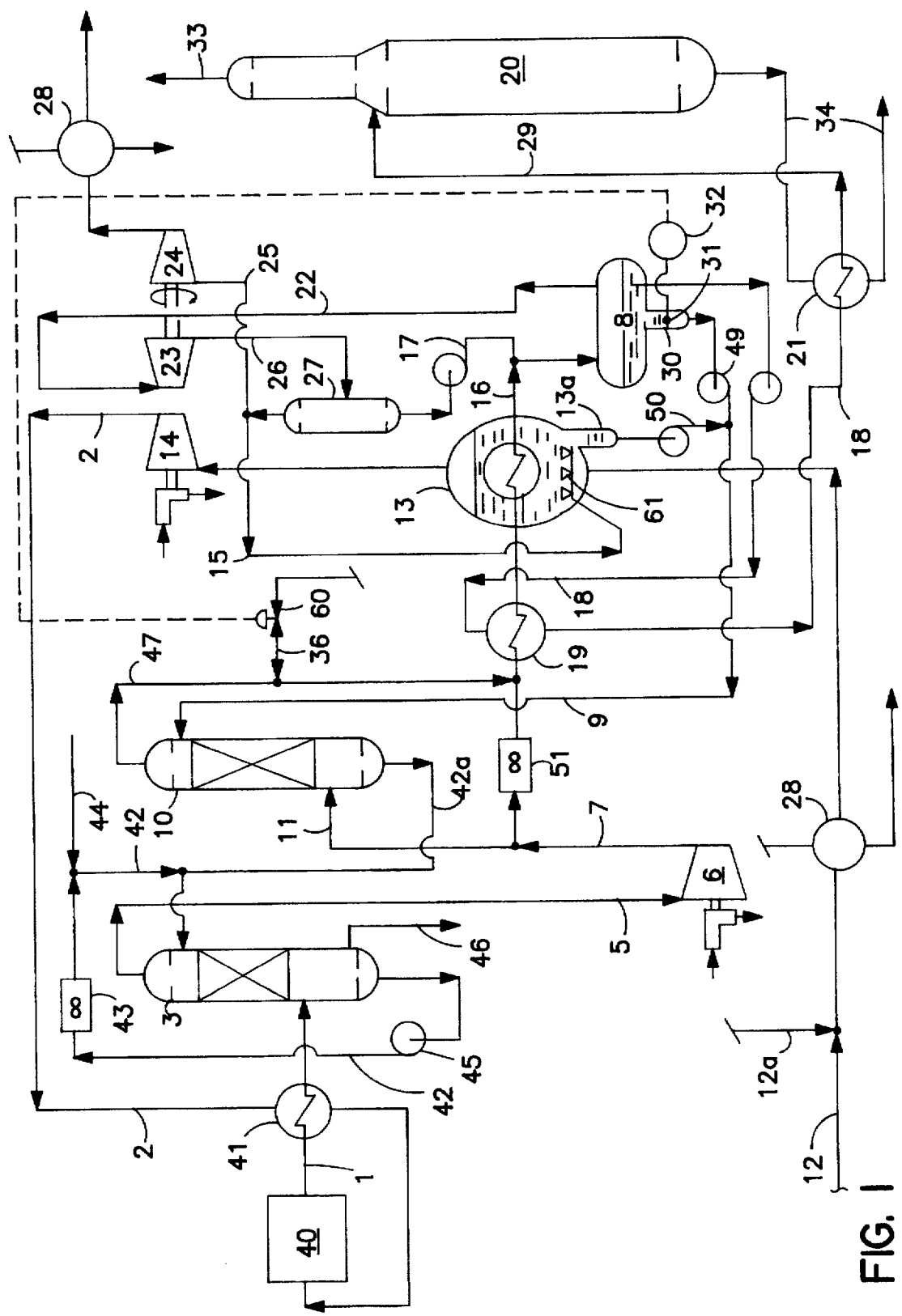
FIG. 1 is a schematic flowsheet of a unit for dehydrogenating a cut containing isobutane at 93% comprising the device for inhibiting water according to the invention and a system for self-cooling of the effluent.

The invention also relates to the catalytic dehydrogenation unit comprising in combination a dehydrogenation reactor (40) delivering an effluent containing water, means (12, 2) for feeding a hydrocarbon charge connected to an input of the reactor, at least one means (41) for cooling an effluent connected to an output of the reactor, means (6) for compressing the effluent, means for inhibiting the water contained in the effluent, means (13) for cooling the compressed effluent connected to means for inhibiting water, means (8) for separating the cooled effluent connected to the cooling means, means (22, 18) for recovering a hydrogen-rich phase and a liquid phase containing olefinic hydrocarbons.

Figure 2:
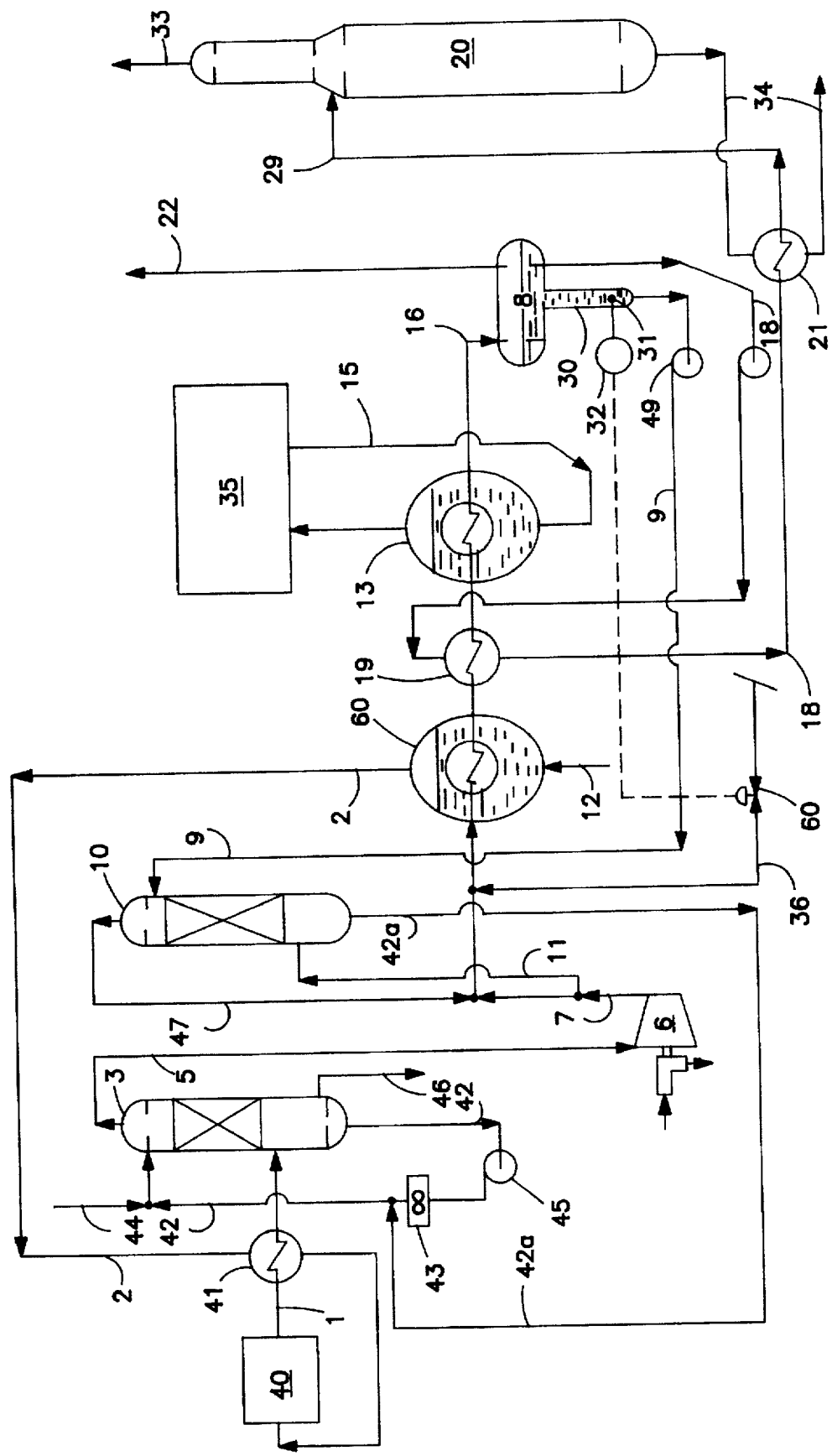
FIG. 2 is a schematic flowsheet of dehydrogenation unit comprising the device for inhibiting water according to the invention and a system for external cooling of the effluent.

More specifically, as shown in FIG. 1 and FIG. 2, the unit is characterized in that it comprises:

means for water saturation of at least one part of the effluent comprising a chamber (3) having a suitable packing, of elongated shape which comprises at one end a first input connected to an effluent feed (1), a first water output connected to means (42, 45) for recycling the water, at the other end a second input connected to means (42) for recycling the water and a second output (5) delivering the water-saturated effluent, and means for inhibiting the freezing of water comprising a stripping column (10) having a suitable packing, preferably structured, and having at the first end a first input (11) of the water-saturated effluent connected to the second output of chamber (3) for water saturation of the effluent, a first output connected to means (42a) for recycling the water to saturation chamber (3) and at an opposite end, a second input connected to means (9) for recycling an aqueous liquid phase containing solvent connected to said separating means (8) suited to deliver said aqueous liquid phase and a second output (47) connected to means (13) for cooling the effluent.

According to a first variant of the unit, the first input of the saturation chamber is connected to said means (41) for cooling the effluent, the second output of the saturation chamber is connected to an input of compression means (6) and the first input of the water-saturated effluent in stripping column (10) is connected to an output (7) of the compression means.

Furthermore, the output of the compression means can further be connected to the means for cooling the effluent when the whole of the effluent does not pass through the stripping column.

According to a second variant of the unit, the means for cooling the effluent at the output of the reactor can be connected to an input of the compression means, the first input of saturation chamber (3) is connected to an output of compression means (6) and the second output of saturation chamber (3) is connected directly to the first input of stripping column (10).

Furthermore, the second output of the saturation chamber can further be connected to the cooling means when the whole of the effluent does not pass through the stripping column.

Generally, the charge can comprise paraffinic hydrocarbons with 3, 4 and/or 5 carbon atoms. More specifically, it can comprise isobutane.

It can be introduced in liquid form or in gaseous form, in the presence or not of recycled hydrogen.

In relation to the dehydrogenation units according to the prior art, this invention exhibits the advantage of requiring pressure levels, both in the dehydrogenation reactor and in the compression devices, much lower because of the slight pressure drops due to the devices for water saturation and therefore for direct quenching of the effluent, and for inhibition of the water by the use of solvents. Under these conditions, conversion rates greater than those of the prior art result if the procedure can be performed in the dehydrogenation reactor at lower pressure levels.

The devices for cooling the effluent for the purpose of its separation into gas (hydrogen) and into liquid (unconverted, paraffinic olefins and hydrocarbons) can be external (indirect exchange with propane, for example).

According to another particularly advantageous variant, they can comprise a dual-chamber heat exchanger, of which the first chamber is fed by the liquid charge without or with at least one part of the recycled hydrogen coming from the separating means, this hydrogen furthermore able to be expanded before its input in the first chamber of the heat exchanger. The evaporation of the charge with or without hydrogen then contributes to the cooling of the effluent in the second chamber of the heat exchanger (tubes or plates, for example).

DETAILED DESCRIPTION OF THE PREFERRED EMBODIMENTS

Isobutane charge 2, in gaseous form, and hydrogen, after having been preheated to a suitable temperature by direct exchange in a plate heat exchanger 41, with slight pressure drop, are introduced into a catalytic dehydrogenation reactor 40 operating at low pressure (1.5 to 1.8 absolute bars) and at high temperature 580–600° C. Effluent 1 which goes out enriched with olefinic hydrocarbons (more than 50%, for example) is cooled by indirect exchange in this plate exchanger, then in another exchanger 3 which is a structured packing column with a large specific surface and height equivalent to about 5 theoretical plates. This column achieves a direct quenching of the effluent at a temperature of about 20° C. to 50° C., saturates the effluent with water and rids it of its impurities.

The effluent is introduced at the lower part of the column (3) goes through the packing upward where it is put in countercurrent contact with a mixture of liquid phases containing water introduced into the upper part of the column, coming in part from a recycling line 42 at the base of column 3 via a pump 45 and at least one air exchanger 43 and in the remaining part from a stripping column 10 from a feed line 42a. Soda (5% by weight approximately) can be introduced by a pipe 44 into line 42 to wash the effluent of its undesirable impurities.

Water can be drawn off from the lower part of the quenching and saturation column by a line 46. The effluent cooled to about 20–50° C. but still superheated is recovered at the column head and feeds, by a line 5, the aspiration of a centrifugal compression system 6 at a pressure considerably higher than the atmospheric pressure. Compression system 6 raises the pressure of the reaction effluent to a value such that an effective separation of a liquid hydrocarbon phase from a hydrogen-rich gas phase becomes possible at a temperature generally less than 0° C. In the case of the dehydrogenation of isobutane, a pressure of 13 to 18 bars is quite suitable. The energy requirements of the compression system can be provided by a gas turbine, a steam turbine or an electric motor.

At the output of compressor 6, a line 7 divides the effluent that is compressed and saturated with water into two flows. A first flow representing 5–10% of the effluent is directed by a line 11 to the lower part of a column 10 for inhibiting freezing of water (or for stripping) containing a structured packing, for example, a SULZER BX packing having 5 to 10 equivalent theoretical plates.

This flow is put in ascending countercurrent contact with a feed 9 of water and of methanol in liquid phase introduced at the column head and coming from a separation chamber 8 defined below.

At the lower output, an aqueous phase no longer containing appreciable solvent, that is recycled at the upper input of saturation column 3, is recovered. At the upper output of the stripping column, a line 47 evacuates a gas phase charged with solvent and hydrocarbon effluent toward the remaining part of the effluent that is compressed, water-saturated and cooled by an air or water heat exchanger 51 and the effluent-methanol-water mixture is cooled by an indirect heat exchange in an exchanger 19 with an effluent 18 from a separation chamber 8 containing olefinic hydrocarbons (more than 50%, for example) and unconverted saturated hydrocarbons. Then, this mixture whose water that is present is inhibited by the presence of methanol is introduced in a suitable amount into a heat exchanger 13 with tubes and with calandria suited to cool the effluent by indirect exchange. Actually, the fresh and unconverted, therefore recycled, liquid isobutane charge is brought by a line 12 in liquid phase and cooled in a heat exchanger 28 at the base of the calandria of heat exchanger 13. The presence of water in the charge can be inhibited by adding methanol 12a into line 12. This liquid phase is evaporated by the heat yielded by the tubes in the presence of at least one part of recycled hydrogen introduced by a line 15 into the calandria, which contributes to reducing its boiling temperature at a given pressure. The hydrogen is introduced at the lower part of the calandria by means 61 suited to promote contact with said liquid phase approximately in the entire space occupied by the latter. Under these conditions, it is used as a cooling fluid. A gas phase is recovered in the upper part of the calandria, comprising evaporated isobutane and hydrogen that is recycled and evacuated by a line 2 in the direction of plate heat exchanger 41 upstream from reactor 40 to cool the effluent. In lower part 13a of the calandria, it is possible to recover a condensate of methanol and water which can be recycled by a line 50 for feed 9 of stripping column 10.

The pressure inside the calandria of heat exchanger 13 suited to cool the effluent and therefore the evaporation pressure is kept at a suitable level by single stage and variable speed compressor 14, which has its input connected directly to the calandria.

To obtain an advantageous range of temperatures of $-25°$ C. to $-10°$ C., the pressure in the calandria is kept at about 2 absolute bars. By this compressor 14, the charge in vapor phase (isobutane and hydrogen) is compressed toward the input of the dehydrogenation reactor at a pressure of 3 to 4 absolute bars.

The effluent cooled in the tubes of heat exchanger 13 goes out through a line 16 at a temperature of about $-20°$ C. to $-25°$ C., for example, and is directed toward a phase separator 8.

At the head of the separator, a line 22 recovers a vapor phase containing mostly hydrogen and a small proportion of hydrocarbons and guides it into a pressure-reducing turbine 23 where it is expanded at constant entropy from a pressure, for example, of 15 bars, to a pressure of about 2.5 bars. At the output of pressure-reducing turbine 23, the temperature in line 26 typically drops, from about $-25°$ C. to $-85°$ C., which causes the condensation of a hydrocarbon liquid phase called cryogenic which is separated from the hydrogen in a separation chamber 27. This liquid phase is recovered at the bottom of chamber 27 by a line 17 and mixed with the cooled effluent going out from cooling heat exchanger 13, at a point upstream from the input of separator 8. This direct contact by suitable means for mixing contributes to cooling the compressed effluent by about 2° C. to 10° C. in addition.

At the Upper part of separation chamber 27, a hydrogen gas phase (more than 98% of hydrogen moles) is recovered, which is divided to form a hydrogen stream intended to be recycled partly by a line 15 and sent first of all into the calandria of cooling heat exchanger 13 to evaporate the liquid isobutane charge. The other part of the hydrogen stream is directed by a line 25 to a compressor 24 set in motion by turbo-pressure reducing valve 23. This hydrogen stream compressed at about 10 bars and at a temperature of $-30°$ C. can be reheated in a heat exchanger 28 placed on line 12 downstream from addition 12a of methanol, by indirect exchange with the liquid isobutane charge, and can thereby contribute to cooling the charge before its evaporation.

At the bottom of the separator, a hydrocarbon liquid phase at about $-25°$ C. and about 15 absolute bars, comprising at least 95% isobutene contained in the effluent, which cools, in a heat exchanger 19, the hydrocarbon effluent before its entry into cooling heat exchanger 13, is recovered by a line 18. The hydrocarbon liquid phase is again reheated in another heat exchanger 21 before being introduced into a stabilization column 20 delivering, at the head of the gas fuel oil by a line 33 and at the bottom by a line 34, isobutene and unconverted isobutane which contribute to the heat exchange in exchanger 21 and that are sent to an MTBE forming unit (not shown).

Furthermore, a decanted liquid phase of water containing 20–70% by weight of methanol that is recycled by a line 9 and a pump 49 to the upper input of the stripping column is recovered in a chamber 30 at the bottom of separator 8.

The concentration of methanol to be introduced into the hydrocarbon effluent having to be cooled can be continuously controlled by a densimeter 31 immersed in decantation chamber 30 of separator 8 which makes possible measure of density, from which concentration can be determined. The densimeter is connected to a microcomputer 32 which controls, by comparison with a range of previously recorded concentrations, a valve 60 for opening or closing a feed pipe 36 of a fluid containing methanol, to line 47.

According to FIG. 2, which illustrates a variant of the unit for catalytic dehydrogenation of an isobutane cut, the device for saturation and for inhibition of water by methanol is identical to that represented in FIG. 1 with the same references. The case has been described, however, where the liquid isobutane charge is introduced by line 12 into a heat exchanger 60 where it is evaporated in the absence of hydrogen by indirect exchange with the hydrocarbon effluent coming from the dehydrogenation reactor and containing the suitable methanol proportion according to the invention.

The effluent is again cooled in heat exchanger 19 by indirect exchange with the olefins and the unconverted hydrocarbons coming from separator 8 by line 18 then is cooled between $-20°$ C. and $-40°$ C. in an indirect heat exchanger 13 by an external cooling device 35, for example, with propane, before being routed to separator 8 by line 16. The hydrogen is recovered at the head by line 22, while the olefins and gas fuel oil are recovered by line 18 to be separated in stabilization column 20.

The decanted phase in lower chamber 30 of separator 8 containing the water and methanol liquid phase is recycled as described above by line 9 to stripping column 10.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents, and publications, cited above and below, and of corresponding French Application No. 92/13.516, filed Nov. 6, 1992, are hereby incorporated by reference.

We claim:

1. A catalytic dehydrogenation unit comprising in combination a dehydrogenation reactor (40) delivering an effluent containing water, means (12, 2) for feeding a hydrocarbon charge connected to an input of the reactor, at least one means (41) for cooling an effluent connected to an output of the reactor, means (6) for compressing the effluent, means for inhibiting the water contained in the effluent, means (13) for cooling the compressed effluent connected to the means for inhibiting the water, means (8) for separating the cooled effluent connected to the cooling means, means (22, 18) for recovering a hydrogen-rich phase and a liquid phase containing olefinic hydrocarbons, said unit comprising:

means for water saturation of the effluent comprising an elongated chamber having a suitable packing (3), which comprises at one end a first input connected to an effluent feed (1), a first water output connected to means (42, 45) for recycling the water, at the other end a second input connected to means (42) for recycling the water and a second output (5) delivering the water-saturated effluent, and means for inhibiting the water comprising a stripping column (10) having a packing, and having at a first end a first input (11) of the water-saturated effluent connected to the second output of chamber (3) for water saturation of the effluent, a first output connected to means (42a) for recycling the water to saturation chamber (3) and at an opposite end, a second input connected to means (9) for recycling an aqueous liquid phase containing solvent connected to said separating means (8) suited to deliver said aqueous liquid phase and a second output (47) connected to means (13) for cooling the effluent.

2. A dehydrogenation unit according to claim 1, wherein the first input of saturation chamber (3) is connected to said means (41) for cooling the effluent, the second output of the saturation chamber is connected to an input of compression means (6) and the first input of the water-saturated effluent in stripping column (10) is connected to an output (7) of the compression means.

3. A dehydrogenation unit according to claim 1, wherein means (41) for cooling the effluent are connected to an input of compression means (6), the first input of saturation chamber (3) is connected to an output of compression means (6), and the second output of saturation chamber (3) is connected directly to the first input of stripping column (10).

4. A dehydrogenation unit according to claim 3, wherein the second output of saturation chamber (3) is further connected to the cooling means.

5. A dehydrogenation unit according to claim 2, wherein the output of compression means (6) is further connected to cooling means (13).

6. Dehydrogenation unit according to claim 1, wherein the cooling means comprise a dual-chamber indirect heat exchanger, the first chamber comprising a feed (12) of liquid charge, or optionally a feed (15) of gaseous recycled hydrogen, said first chamber being suited to evaporate the charge and to cool said second chamber where the effluent circulates by indirect exchange and further comprising an output connected to means (2) for feeding reactor (40).

7. A dehydrogenation unit according to claim 1, wherein the means for cooling the effluent comprise a heat exchanger (13, 35) using an external cooling fluid.

8. A dehydrogenation unit according to claim 1, wherein means (42, 45) for recycling water to the saturation chamber comprise at least one means (43) for cooling the water.

9. A catalytic dehydrogenation unit comprising in combination a dehydrogenation reactor (40) delivering an effluent containing water, a feeder (12, 2), a hydrocarbon charge connected to an input of the reactor, at least one effluent cooler (41) connected to an output of the reactor, a compressor (6) for the effluent, an inhibitor for the water contained in the effluent, a cooler (13) for the compressed effluent connected to the inhibitor for the water, a separator (8) for the cooled effluent connected to the cooler (22, 18) for recovering a hydrogen-rich phase and a liquid phase containing olefinic hydrocarbons, said unit comprising:

a water saturator for the effluent comprising an elongated chamber having packing (3), which comprises at one end a first input connected to an effluent feed (1), a first water output connected to a water recycle (42, 45) at the other end a second input connected to water recycle (42) and a second output (5) delivering the water-saturated effluent, and an inhibitor for the water comprising a stripping column (10) having packing, and having at a first end a first input (11) of the water-saturated effluent connected to the second output of chamber (3) for water saturation of the effluent, a first output connected to water recycle (42a) the water to saturation chamber (3) and at an opposite end, a second input connected to solvent-containing aqueous liquid phase recycle (9) connected to said separator (8) suited to deliver said aqueous liquid phase and a second output (47) connected to cooler (13) for the effluent.

* * * * *